United States Patent [19]
Räduchel et al.

[11] 3,970,692
[45] July 20, 1976

[54] PROCESS FOR THE PREPARATION OF PROSTAGLANDIN $F_{2\alpha}$ AND THE ANALOGS THEREOF

[75] Inventors: Bernd Räduchel; Werner Skuballa; Helmut Vorbrüggen, all of Berlin, Germany

[73] Assignee: Schering Aktiengesellschaft, Berlin & Bergkamen, Germany

[22] Filed: May 23, 1974

[21] Appl. No.: 472,737

[30] Foreign Application Priority Data
May 30, 1973 Germany............................ 2328131

[52] U.S. Cl................. 260/514 D; 260/24 R; 260/346.2 R; 260/413; 260/468 D; 260/520 C
[51] Int. Cl.²....................................... C07C 177/00
[58] Field of Search............... 260/468 D, 514 D, 69

[56] References Cited
OTHER PUBLICATIONS

Fiezen et al., Reagents for Organic Synthesis, pp. 261–262, 621–622, 123842, (1967).
Corey et al., JACS, 92, 397, (1970).
Corey, Proceedings of the Robert A. Welsh Foundation, Conference on Chemical Research XII, Organic Synthesis, 1969, p. 76.

*Primary Examiner*—Robert Gerstl
*Attorney, Agent, or Firm*—Millen, Raptes & White

[57] ABSTRACT

Prostaglandin $F_{2\alpha}$ and analogs thereof of the formula

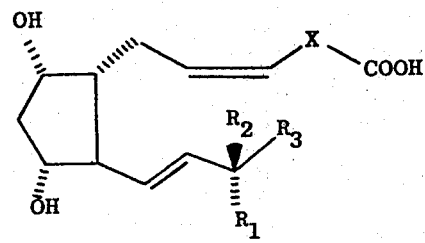

wherein one of $R_1$ and $R_2$ is hydroxy and the other is H or $CH_3$, $R_3$ is the remainder of the lower side chain and X is the remainder of the upper side chain thereof are produced in two steps from a 3-acyloxy mono ester of a lactone of the formula

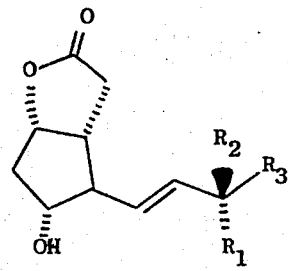

wherein $R_1$, $R_2$ and $R_3$ have the values given below, by reacting the lactone with excess diisobutylaluminum hydride and reacting the thus-produced ketol, in the presence of strong anhydrous base, with a Wittig reagent of the formula $Ph_3P=CH-X-COOH$ wherein Ph is a phenyl group and X has the values given above.

10 Claims, No Drawings

PROCESS FOR THE PREPARATION OF PROSTAGLANDIN F₂ α AND THE ANALOGS THEREOF

BACKGROUND OF THE INVENTION

This invention relates to a novel process for the production of prostaglandin $F_{2\alpha}$ and its analogs.

According to the procedure of E. J. Corey et al., J. Am Chem. Soc., Vol. 93 (1971), p. 1491, the lactone of the formula

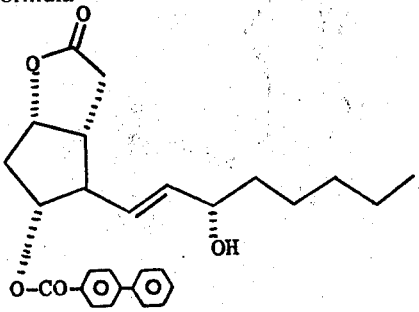

is converted into prostaglandin $F_{2\alpha}$ in several steps, according to the following reaction scheme:

In the above reaction scheme, BP = p-biphenyl and THP = tetrahydropyranyl-2.

After saponification (a) of the lactone of Formula I, the bis(tetrahydropyranyl) ether (III) is produced with dihydropyran in the presence of p-toluenesulfonic acid (b). The reduction of the lactone (III) with diisobutylaluminum hydride (c) results in the production of lactol of Formula IV. By means of the Wittig reagent from 4-carboxybutyltriphenylphosphonium bromide and methylsodiummethanesulfinyl (d), the intermediate product of Formula V is obtained, resulting in $PGF_{2\alpha}$ (VI) by hydrolysis (e) of the tetrahydropyranyl groups.

The above-described synthesis comprises five stages, proceeding by way of intermediate products which are sensitive to acids and thus difficult to handle.

It is an object of this invention to provide a simplified process for the preparation of the physiologically valuable prostaglandin $F_{2\alpha}$ and the analogs thereof.

It has now been found, according to the process of this invention, which is suitable for the production of prostaglandin $F_{2\alpha}$ and the analogs thereof, that three steps of the five stage conventional synthesis can be eliminated.

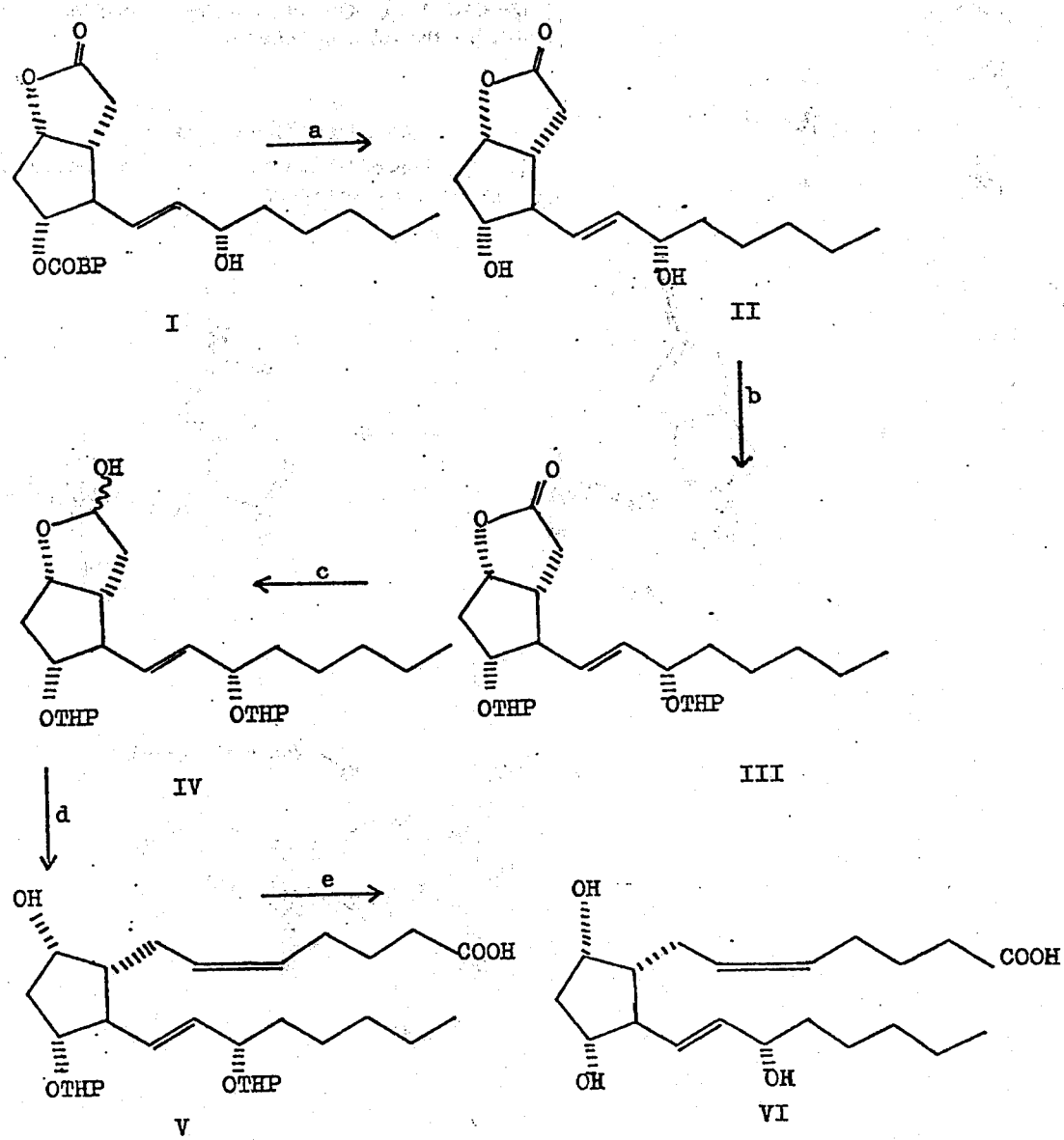

SUMMARY OF THE INVENTION

According to this invention, prostaglandin $F_{2\alpha}$ and the analogs thereof of the formula

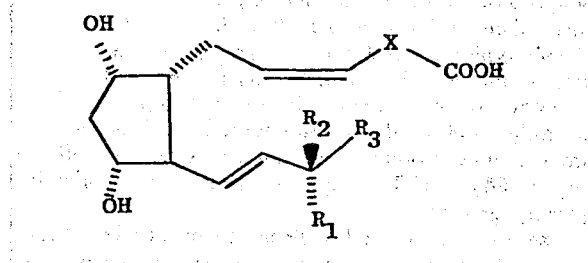

wherein one of $R_1$ and $R_2$ is a hydroxy group and the other is a hydrogen atom or methyl and $R_3$ and X are the remainders of the side chains of prostaglandin $F_{2\alpha}$ or an analog of prostaglandin $F_{2\alpha}$, are produced by treating a 3-acyloxy monoester of a lactone of the general formula

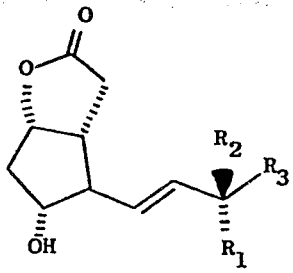

wherein $R_1$, $R_2$ and $R_3$ have the values given above, is treated with excess diisobutylaluminum hydride, and then reacting the thus-obtained lactol of the general formula

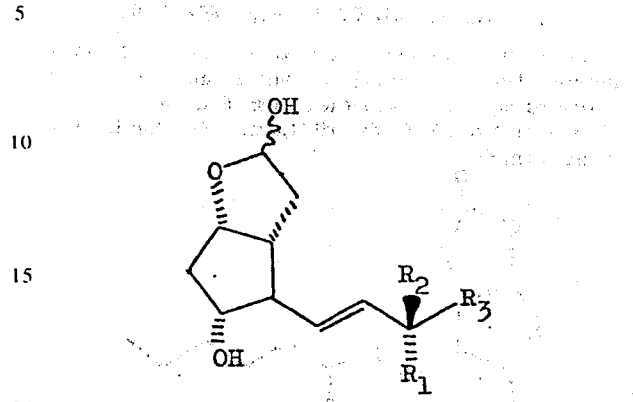

wherein $R_1$, $R_2$ and $R_3$ have the values given above, with a Wittig reagent of the general formula $Ph_3P=CH-X-COOH$ wherein Ph is a phenyl group and X has the values given above.

DETAILED DISCUSSION

The reactions of this invention can be illustrated by the following reaction scheme:

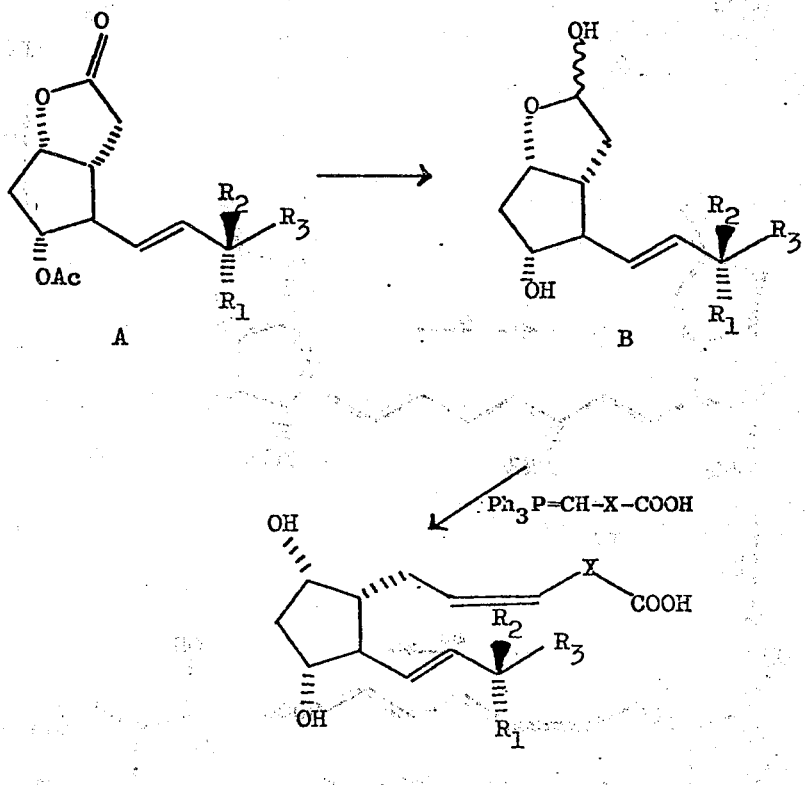

In the first step of the process of this invention, a lactone monoester of general Formula A is treated with excess, e.g., 3 to 6, preferably 4 to 5 molar excess, diisobutylalumunim hydride. The reaction can be conducted at temperatures of from −100° to 0° C., preferably −80° to −40° C. The reaction is conducted in an aprotic solvent, e.g., toluene, diethyl ether, tetrahydofuran or glyme. During this treatment, not only is the lactone group reduced, but the ester group is also split quantitatively with the formation of a triol of general Formula B.

The thus-produced triol of Formula B can be isolated and, if desired, purified in a conventional manner or it can be used without purification after decomposition of the metallocomplex produced in the reaction with the alkyl metallohydride, e.g., with an alcohol and/or water. Since the second reaction is conducted in the absence of water, the starting material should be dry and free from other proton-donating sources.

In Formula A, Ac is the acyl radical of an aliphatic or aromatic carboxylic acid.

It will be apparent to those skilled in the art that because, in the first step of the process of this invention, like the prior art process, the 3-acyloxy group is cleaved to form a free 3-hydroxy group, the exact nature of the esterifying group is not critical. An ester group of a highly hindered carboxylic acid which is therefore resistant to cleavage with diisobutylaluminum hydride obviously should not be selected for this reason. However, the selection of the particular ester group presents no problems since simple esters are preferred.

Examples of acyl radicals of aliphatic carboxylic acids are alkanoyl of 1–12, preferably 2–8, carbon atoms, e.g., acetyl, propionyl, butyryl, valeryl, hexanoyl or heptanoyl. Also suitable are the acyl radicals of long-chain and of branched aliphatic carboxylic acids, including those substituted, e.g., by halo, amino or hydroxy. Also suitable are acyl radicals of aromatic carboxylic acids, especially carbocyclic acids of, e.g., 7–15 carbon atoms and with 1–2 separate or fused aromatic rings, e.g., benzoyl and benzoyl substituted by alkyl of 1–4 carbon automs, alkoxy of 1–4 carbon atoms, nitro, halo, amino, hydroxy or phenyl, e.g., p-toluyl, p-nitrobenzoyl and p-phenylbenzoyl.

In the above formulae one of $R_1$ and $R_2$ is a hydroxy group and the other is a hydrogen atom or methyl.

In the above formulae, $R_3$ is the remainder of the lower, i.e., hydroxy substituted, side chain of prostaglandin $F_{2\alpha}$ or an analog of prostaglandin $F_{2\alpha}$. For example, $R_3$ can be, inter alia, pentyl-, 1-methylpentyl-, 1,1-dimethylpentyl-, heptyl-, n-propoxymethyl-, n-pentyloxymethyl- or phenoxymethyl-. $R_3$ can also be any other organic radical which is stable with respect to the diisobutylaluminum hydride.

The thus-produced triol of general Formula B is then converted with a Wittig reagent into prostaglandin $F_{2\alpha}$ or an analog of prostaglandin $F_{2\alpha}$ of Formula C.

The Wittig reagents are those having the formula $Ph_3P=CH-X-COOH$, wherein Ph is phenyl and X is the remainder of the upper, i.e., —COOH substituted, side chain of prostaglandin $F_{2\alpha}$ or an analog of prostaglandin $F_{2\alpha}$.

Such X groups are straight and branched chain alkylene of 1 to 8 carbon atoms and alkyleneoxy-alkylene of 2–5 carbon atoms, e.g., —(CH$_2$)$_n$, wherein n is an integer from 1 to 5, inclusive, preferably 3, —CH$_2$—O—CH$_2$—,

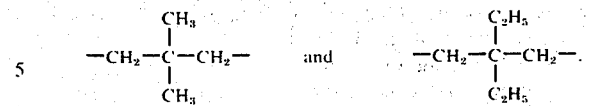

The Wittig reagent can be liberated during the reaction of carboxy-X-triphenylphosphonium bromide, wherein X has the values given above, with an anhydrous strong base, in an aprotic solvent, e.g., dimethyl sulfoxide or dimethylformamide. Examples of suitable anhydrous bases are alkali-metal hydrides, e.g., sodium hydride, alkali-metal alkoxides, e.g., potassium tert.-butylate, alkyl alkali-metals, e.g., butyl-lithium, and other bases capable of forming an alkali metal or alkaline earth salt of metal an aliphatic hydroxy group. The reaction is conducted at temperatures of 0° C. to 100° C., preferably at an elevated temperature, e.g., 30° C to 80° C.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE a. Under a nitrogen atmosphere and at −60° C., 1.0 ml. of a 20% solution of diisobutylaluminum hydride in toluene was added to a solution of 120 mg. of 2-[3α-biphenylcarbonyloxy-5α-hydroxy-2β-(3α-hydroxy-trans-1-octen-1-yl)-cyclopent-1α-yl]-acetic acid γ-lactone in 5 ml. of dry toluene. After 30 minutes, the reaction was terminated by adding 0.5 ml. of isopropyl alcohol dropwise to the reaction mixture. After the addition of 5 ml. of water at 0° C., the mixture was agitated for 15 minutes and then extracted three times with respectively 20 ml. of ethyl acetate. The combined extracts were washed with saturated NaCl solution and dried over magnesium sulfate. After evaporating the solvent under reduced pressure, approximately 120 mg. of 2-[3α, 5α-dihydroxy-2β-(3α-hydroxy-trans-1-octen-1-yl)-cyclopent-1α-yl]-acetaldehyde γ-hemiacetal was obtained in a mixture with a p-phenylbenzyl alcohol.

b. 4.25 ml. of a solution of methylsodium methanesulfinyl in dimethyl sulfoxide (from 106 mg. of sodium hydride and 4.25 ml. of dimethyl sulfoxide at 70° C.) was added to a solution of 1.04 g. of 4-carboxybutyltriphenylphosphonium bromide in 3 ml. of absolute dimethyl sulfoxide.

A solution of 120 mg. of 2-[3α,5α-dihydroxy-2β-(3α-hydroxy-trans-1-octen-1-yl)-cyclopent-1α-yl]-acetaldehyde γ-hemiacetal, in a mixture with p-phenylbenzyl alcohol, in 2 ml. of dimethyl sulfoxide was gradually added dropwise to the above solution, and the mixture was agitated for 2 hours at 50° C.

The reaction mixture was poured on 10 ml. of ice water, extracted three times with ether, and the extract discarded. The aqueous phase was acidified with a 10% citric acid solution to pH 4 and extracted four times with a mixture of ether and hexane (1 : 1). The extract was washed with NaCl solution, dried over magnesium sulfate, and evaporated under reduced pressure. The residue was chromatographed on 10 g of silica gel with chloroformmethanol (5 : 1), thus obtaining 60 mg. of pure prostaglandin $F_{2\alpha}$. Yield: 63%.

In accordance with the above example, the following prostaglandin analogs:
16-methyl-prostaglandin $F_{2\alpha}$,
16,16-dimethyl-prostaglandin $F_{2\alpha}$,
(15S)-15-methyl-prostaglandin $F_{2\alpha}$,
(15R)-15-methyl-prostaglandin $F_{2\alpha}$,
20-ethyl-prostaglandin $F_{2\alpha}$,
17-oxa-prostaglandin $F_{2\alpha}$,
17-oxa-20-ethyl-prostaglandin $F_{2\alpha}$, and
16-phenoxy-17,18,19,20-tetra-nor-prostaglandin $F_{2\alpha}$
can be prepared from
2-[3α-biphenylcarbonyloxy-5α-hydroxy-2β-(3α-hydroxy-4-methyl-trans-1-octen-1-yl)-cyclopent-1α-yl]-acetic acid γ-lactone,
2-[3α-biphenylcarbonyloxy-5α-hydroxy-2β-(3α-hydroxy-4,4-dimethyl-trans-1-oceten-1-yl)-cyclopent-1α-yl]-acetic acid γ-lactone,
2-[3α-biphenylcarbonyloxy-5α-hydroxy-2β-(3α-hydroxy-3β-methyl-trans-1-octen-1-yl)-cyclopent-1α-yl]-acetic acid γ-lactone,
2-[3α-biphenylcarbonyloxy-5α-hydroxy-2β-(3β-hydroxy-3α-methyl-trans-1-oceten-1-yl)-cyclopent-1α-yl]-acetic acid γ-lactone,
2-[3α-biphenylcarbonyloxy-5α-hydroxy-2β-(3α-hydroxy-trans-1-decen-1-yl)-cyclopent-1α-yl]-acetic acid γ-lactone,
2-[3α-biphenylcarbonyloxy-5α-hydroxy-2β-(3α-hydroxy-4-n-propoxy-trans-1-buten-1-yl)-cyclopent-1α-yl]-acetic acid γ-lactone,
2-[3α-biphenylcarbonyloxy-5α-hydroxy-2β-(3α-hydroxy-4-n-pentyloxy-trans-1-buten-1-yl)-cyclopent-1α-yl]-acetic acid γ-lactone,
2-[3α-biphenylcarbonyloxy-5α-hydroxy-2β-(3α-hydroxy-16-phenoxy-trans-1-buten-1-yl)-cyclopent-1α-yl]-acetic acid γ-lactone,
respectively.

The preceding example can be repeated with similar success by substituting the generically and specifically described reactants and/or operating conditions of this invention for those used in the preceding example.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. In a process for the production of prostaglandin $F_{2\alpha}$ and analogs thereof of the formula

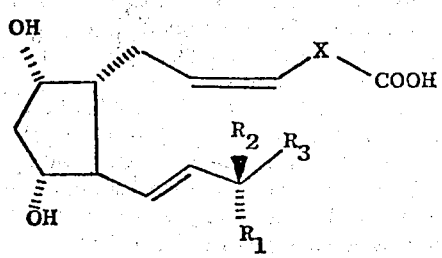

wherein one of $R_1$ and $R_2$ is a hydroxy group and the other is a hydrogen atom or methyl, $R_3$ is alkyl of 5–7 carbon atoms, alkoxy of 3–5 carbon atoms or phenoxy and X is alkylene of 1–8 carbon atoms or alkyleneoxyalkylene of 2–5 carbon atoms, from a 3-ester of an aliphatic carboxylic acid of 1–12 carbon atoms or an aromatic carboxylic acid of 7–15 carbon atoms and with 1–2 separate or fused rings and of a lactone of the general formula

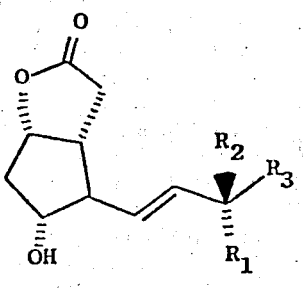

wherein $R_1$, $R_2$ and $R_3$ have the values given above, the improvement which comprises treating the lactone monoester with an excess of diisobutylaluminum hydride at −100° to 0° C., to produce a lactol of the formula

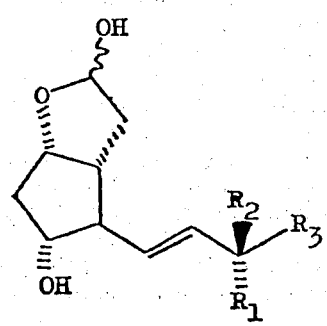

wherein $R_1$, $R_2$ and $R_3$ have the values given above, and reacting the thus-produced lactol with a Wittig reagent of the formula $Ph_3P=CH-X-COOH$ wherein Ph is phenyl and X has the values given above.

2. A process according to claim 1 wherein $R_1$ is OH, $R_2$ is H and $R_3$ is n-pentyl.

3. A process according to claim 1 wherein X is $-(CH_2)_3-$.

4. A process according to claim 1 wherein the starting compound is 2-[3α-biphenylcarbonyloxy-5α-hydroxy-2β-(3α-hydroxy-trans-1-octen-1-yl)-cyclopent-1α-yl]-acetic acid γ-lactone.

5. A process according to claim 4 wherein X is $-(CH_2)_3-$.

6. A process according to claim 1 wherein in the first step, the lactone is treated with a 3 to 6 molar excess of diisobutylaluminum hydride.

7. A process according to claim 4 wherein in the first step, the lactone is treated with a 3 to 6 molar excess of diisobutylaluminum hydride.

8. A process of claim 1 wherein X is 1,3-propylene, 2-oxa-1,3-propylene, 2,2-dimethyl-1,3-propylene or 2,2-diethyl-1,3-propylene, $R_3$ is pentyl-, 1-methylpentyl-, 1,1-dimethylpentyl-, heptyl-, n-propoxymethyl-, n-pentyloxymethyl or phenoxymethyl-, the 3-ester is an ester of an alkanoic acid of 2–8 carbon atoms or a carbocyclic carboxylic acid of 7–15 carbon atoms and 1–2 aromatic rings.

9. A process of claim 1 wherein the first step is conducted at −80° to −40° C. with a 3 to 6 molar excess of diisobutylaluminum hydride.

10. A process according to claim 9 wherein the starting compound is 2-[3α-biphenylcarbonyloxy-5α-hydroxy-2β-(3α-hydroxy-trans-1-octen-1-yl)-cyclopent-1α-yl]-acetic acid γ-lactone.

* * * * *

UNITED STATES PATENT AND TRADEMARK OFFICE
CERTIFICATE OF CORRECTION

PATENT NO. : 3,970,692
DATED : July 20, 1976
INVENTOR(S) : Raduchel; Skuballa; Vorbruggen It is certified that error appears in the above-identified patent and that said Letters Patent is hereby corrected as shown below:

Column 7, claim 1, line 6, reads "alkoxy" should read --alkoxymethyl--.

Column 7, claim 1, line 6, reads "phenoxy" should read "--phenoxymethyl--.

Signed and Sealed this

Twenty-fourth Day of September 1985

[SEAL]

Attest:

Attesting Officer

DONALD J. QUIGG

Commissioner of Patents and Trademarks—Designate